United States Patent [19]

O'Lenick, Jr.

[11] Patent Number: 5,581,001
[45] Date of Patent: Dec. 3, 1996

[54] BRANCHED ESTERS

[75] Inventor: Anthony J. O'Lenick, Jr., Lilburn, Ga.

[73] Assignees: Siltech Inc., Norcross, Ga.; Biosil Technologies, Paterson, N.J.

[21] Appl. No.: 421,518

[22] Filed: Apr. 13, 1995

[51] Int. Cl.$^6$ .................................................. C07C 53/26
[52] U.S. Cl. ........................................................... 554/227
[58] Field of Search .............................................. 554/227

[56]         References Cited

U.S. PATENT DOCUMENTS 4,425,458  1/1984  Lindner et al. .
4,868,236  9/1989  O'Lenick .

OTHER PUBLICATIONS

Chemical Abstracts, 82: 139146, 1973.

*Primary Examiner*—Gary Geist
*Assistant Examiner*—Deborah D. Carr

[57]            ABSTRACT

The present invention deals with the certain novel esters which are prepared by the reaction of an alpha methyl alcohol and a fatty acid. These materials are useful as lubricating oils where outstanding liquidity, resistance to oxidation, and minimal variation in viscosity as a function of temperature is required. This combination of properties make these compounds excellent candidates as additives to synthetic lubricating oil and extreme pressure additives.

10 Claims, No Drawings

BRANCHED ESTERS

BACKGROUND OF THE INVENTION

1. Field of the Invention

The present invention deals with the certain novel esters of highly purified branched alcohols which are prepared by the reaction of a pure alpha methyl alcohol and a fatty acid. These materials are useful as viscosity index modifiers and lubricating oils where outstanding liquidity, resistance to oxidation, and minimal variation in viscosity as a function of temperature is required. This combination of properties make these compounds excellent candidates as additives to synthetic lubricating oil and extreme pressure additives.

2. Description of the Art Practices

Guerbet alcohols have been known for many years. Over the years there have been a number of derivatives patented. U.S. Pat. 4,868,236 to O'Lenick discloses a guerbet citric ester and polymers thereof useful in plastic lubrication. U.S. Pat. 4,425,458 to Lindner and O'Lenick teaches that specific guerbet esters can be used as polycarbonate lubricants.

Guerbet alcohols are regio specific beta branched alcohols. A typical guerbet alcohol conforms to the following structure:

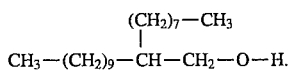

This substitution pattern gives liquidity, but the compounds of the present invention provide compounds which have much less variation in viscosity as a function of temperature than the same product derived from guerbet alcohols.

THE INVENTION

This invention relates to a particular group of esters made by the reaction of a high purity alpha methyl substituted alcohol and a fatty acid. Additional aspects of the invention is the application of these materials as lubricating oils were the specific properties of the ester results in superior liquidity, lubricity, improved viscosity index modification and oxidative stability.

An additional aspect of the invention is esters made by the reaction of the high purity alpha methyl alcohol and specific guerbet acids, which are themselves highly branched. Esters so obtained not only have little variation in viscosity as a function of temperature, but are also very low in initial viscosity. This combination of properties make these esters extremely valuable as viscosity index modifiers.

The compounds of the current invention are conform to the following structure;

$$R-C(O)-O-(EO)_a-(PO)_b(EO)_c-R'$$

wherein;
R is selected from the group consisting of $$CH_3-(CH_2)_d-$$

and

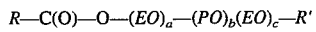

d is an integer ranging from 4 to 18;
e is an integer ranging from 1 to 16;

f is an integer ranging from 1 to 16;
EO is $(CH_2-CH_2-O)$;
PO is $(CH_2-CH(CH_3)-O-)$;
R' is

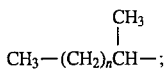

n is an integer ranging from 5 to 17;
a, b, and c are independently integers ranging from 0 to 20.

The alpha methyl alcohol is a critical ingredient for the performance of the compounds of the present invention. The availability of purified alpha methyl alcohols is a recent development. We have determined that the purity of the branched alcohol needs to be 80% by weight or greater to function in our application. If the concentration is lower, the viscosity variation as a function of temperature varies too greatly.

Alpha methyl alcohols exist as minor ingredients in oxo alcohols. These alcohols are made by the hydroformylation reaction of olefins using carbon monoxide and hydrogen according to the following reaction:

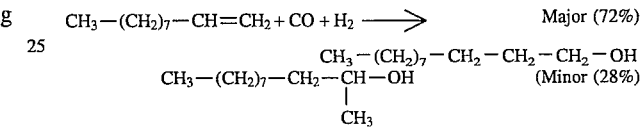

The synthesis of the compounds of the present invention using these alcohols mixed alcohols results in products which do not have the desired properties, because in part the properties of the major alcohols mask the properties of the minor alcohols. It is necessary to get the purity of the minor component up to 80% for the desired properties to appear in our application. Heretofore the purity desired was not available.

PREFERRED EMBODIMENTS

In a preferred embodiment a, b, and c are each o.

In another preferred embodiment a, b, and c are each greater than 0.
In another preferred embodiment R is

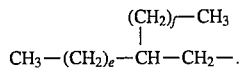

In another preferred embodiment b ranges from 2 to 10.
In another preferred embodiment n ranges from 9 to 15.
In another preferred embodiment d ranges from 10 to 16.

RAW MATERIAL EXAMPLES

| Fatty Acids $CH_3-(CH_2)_d-C(O)-OH$ | |
|---|---|
| Example | d |
| A | 4 |
| B | 6 |
| C | 8 |
| D | 10 |
| E | 12 |
| F | 14 |
| G | 16 |
| H | 18 |

These materials are commercially available from a variety of sources such Henkel Corporation, Ambler Pa.

GUERBET ACIDS

A preferred ester is prepared using guerbet acids. Guerbet alcohols are oxidized into acids having the same regio specific beta branched properties. These properties present both in the acid and alcohol make products useful in the present invention.

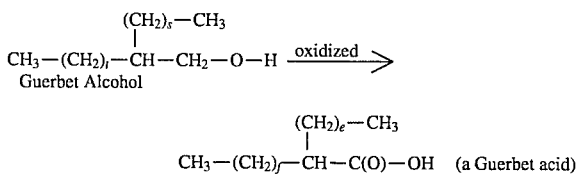

Vista Chemical practices the oxidation of guerbet alcohols commercially. The values of f and e were actually determined by analysis and are not dependant upon trade name for meaning.

| Example | Commercial Name | f | e |
| --- | --- | --- | --- |
| I | Isocarb 10 | 3 | 3 |
| J | Isocarb 12 | 4 | 4 |
| K | Isocarb 14 | 5 | 5 |
| L | Isocarb 16 | 6 | 6 |
| M | Isocarb 18 | 7 | 7 |
| N | Isocarb 20 | 8 | 8 |
| O | Isocarb 32 | 14 | 14 |

Isocarb is a trademark of Vista.

BRANCHED ALCOHOLS

This critical ingredient is available from Biosil Technologies of Englewood, N.J.. They are all over 80% purity. We have determined that the purity of 80% is critical to performance.

$$CH_3-(CH_2)_n\underset{\underset{CH_3}{|}}{CH}-OH$$

| Example | a | b | c | n |
| --- | --- | --- | --- | --- |
| 1 | 0 | 0 | 0 | 5 |
| 2 | 0 | 5 | 0 | 6 |
| 3 | 20 | 20 | 20 | 7 |
| 4 | 5 | 0 | 0 | 8 |
| 5 | 1 | 6 | 3 | 9 |
| 6 | 20 | 20 | 20 | 10 |
| 7 | 5 | 2 | 5 | 11 |
| 8 | 2 | 2 | 2 | 12 |
| 9 | 0 | 0 | 0 | 13 |
| 10 | 5 | 0 | 0 | 14 |
| 11 | 0 | 10 | 5 | 15 |
| 12 | 0 | 20 | 0 | 16 |
| 13 | 0 | 0 | 0 | 17 |

It will be understood that the alcohols listed above can be used as shown or combined with each other than used to synthesize the ester.

ESTER SYNTHESIS

The esterification reaction is carried out using an excess of alcohol or acid or more typically using an equivalent of each. The esterification reaction can be carried out with or without catalyst, however when no catalyst is used the reaction times are protracted. Catalysts like benzene sulfonic acid, tin, sulfuric acid, tin salts and the like can be used. The most satisfactory catalyst is stannous oxylate.

GENERAL PROCEDURE

To the specified number of grams of alcohol (examples 1–13) is added the specified number of grams of the specified acid (Examples A–O ). Next add 0.1% stannous oxylate based upon the total weight of the batch after all ingredients have been charged, under agitation. The temperature of the mass is raised to 180°–200° C. and water is stripped off as formed. The acid value and hydroxyl value drop to vanishingly small values, and the saponification value increases to theoretical.

The products are clear liquids and are liquid to extraordinary temperatures. They exhibit outstanding lubrication properties and are outstanding viscosity index modifiers.

| | Alcohol | | Acid | |
| --- | --- | --- | --- | --- |
| Example | Example | Grams | Example | Grams |
| 14 | 1 | 130.0 | A | 116.0 |
| 15 | 2 | 439.0 | B | 144.0 |
| 16 | 3 | 2036.0 | C | 172.0 |
| 17 | 4 | 392.0 | D | 200.0 |
| 18 | 5 | 716.0 | E | 228.0 |
| 19 | 6 | 3140.0 | F | 256.0 |
| 20 | 7 | 772.0 | G | 284.0 |
| 21 | 8 | 552.0 | H | 312.0 |
| 22 | 9 | 242.0 | I | 171.0 |
| 23 | 10 | 476.0 | J | 199.0 |
| 24 | 11 | 1080.0 | K | 227.0 |
| 25 | 12 | 1464.0 | L | 255.0 |
| 26 | 13 | 298.0 | M | 283.0 |
| 27 | 1 | 130.0 | N | 311.0 |
| 28 | 2 | 439.0 | O | 479.0 |

The compounds of the invention have viscosities which vary minimally over a wide temperature range. The products made with the guerbet acid are the most preferred since they have minimal viscosity variation and are the lowest viscosity for the number of carbon atoms present.

I claim:

1. A branched ester conforming to the following structure:

$$R-C(O)-O-(EO)_a-(PO)_b(EO)_c-R'$$

wherein;

R is selected from the group consisting of $$CH_3-(CH_2)_d-$$

and $$CH_3-(CH_2)_e-\underset{\underset{(CH_2)_f-CH_3}{|}}{CH}-CH_2-;$$

d is an integer ranging from 4 to 18;
e is an integer ranging from 1 to 16;
f is an integer ranging from 1 to 16;
EO is $(CH_2-CH_2-O)$;
PO is $(CH_2-CH(CH_3)-O-)$;
R' is $$CH_3-(CH_2)_n\underset{\underset{CH_3}{|}}{CH}-;$$

n is an integer ranging from 5 to 17;

a, b, and c are independently integers ranging from 1 to 20.

2. A compound of claim 1 wherein n ranges from 9 to 15.

3. A compound of claim 1 wherein d ranges from 10 to 16.

4. A compound of claim 1 wherein R is

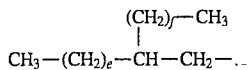

5. A branched ester conforming to the following structure:

$$R-C(O)-O-(EO)_a-(PO)_b(EO)_c-R'$$

wherein;

R is selected from the group consisting of

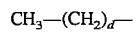

and

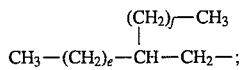

d is an integer ranging from 4 to 18;

e is an integer ranging from 1 to 16;

f is an integer ranging from 1 to 16;

EO is $(CH_2-CH_2-O)$;

PO is $(CH_2-CH(CH_3)-O-)$;

R' is

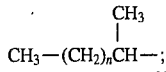

n is an integer ranging from 9 to 17;

a, b, and c are independently integers ranging from 0 to 20.

6. A compound of claim 5 wherein n ranges from 9 to 15.

7. A compound of claim 5 wherein d ranges from 10 to 16.

8. A compound of claim 5 wherein R is

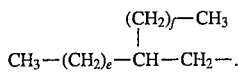

9. A compound of claim 5 wherein a, b, and c are each o.

10. A compound of claim 5 wherein a, b, and c are each greater than 0.

* * * * *